United States Patent [19]

Chao et al.

[11] Patent Number: 4,544,778
[45] Date of Patent: Oct. 1, 1985

[54] BULK SEPARATION OF SORBITOL BY SELECTIVE ADSORPTION ON ZEOLITIC MOLECULAR SIEVES

[75] Inventors: Chien C. Chao, Millwood; John D. Sherman, Chappaqua, both of N.Y.

[73] Assignee: Union Carbide Corporation, Danbury, Conn.

[21] Appl. No.: 645,215

[22] Filed: Aug. 29, 1984

Related U.S. Application Data

[60] Division of Ser. No. 457,427, Jan. 12, 1983, Pat. No. 4,482,761, which is a continuation-in-part of Ser. No. 417,577, Sep. 13, 1982, abandoned.

[51] Int. Cl.$^4$ .................. C07C 29/76; C07C 31/26; C07C 35/16
[52] U.S. Cl. .................. 568/872; 127/46.2; 127/55; 568/833
[58] Field of Search .................. 568/872, 833

[56] References Cited

U.S. PATENT DOCUMENTS 2,524,414 10/1950 Wolfrom et al. .................. 568/872
3,864,406 2/1975 Melaja et al. .................. 568/872
4,069,172 1/1978 Kanaoka et al. .................. 252/455 Z
4,238,243 12/1980 Tu et al. .................. 127/46 B

FOREIGN PATENT DOCUMENTS 7405513 10/1974 Netherlands .................. 568/872

OTHER PUBLICATIONS

Samuelson et al., "Acta Chemica Scandinavica", 22, (1968), pp. 1252–1258.

Primary Examiner—J. E. Evans
Attorney, Agent, or Firm—Richard G. Miller

[57] ABSTRACT

A process for the bulk separation of sorbitol from a solution of a carbohydrate mixture by selective adsorption on a zeolite molecular sieve having a faujasite type structure and having predominantly $Ca^{++}$ cations in association with the $AlO_2^-$ tetrahedra thereof.

6 Claims, 5 Drawing Figures

BULK SEPARATION OF SORBITOL BY SELECTIVE ADSORPTION ON ZEOLITIC MOLECULAR SIEVES

This application is a division of prior U.S. application Ser. No. 457,427 filed Jan. 12, 1983, now U.S. Pat. No. 4,482,761, which is a continuation-in-part of application Ser. No. 417,577 filed Sept. 13, 1982, now abandoned.

BACKGROUND OF THE INVENTION

1. Field of the Invention

This invention relates to a process for the liquid phase separation of inositol and/or sorbitol from mixtures containing same. More particularly and in a preferred embodiment, this invention relates to such a separation by selective adsorption onto certain types of zeolitic molecular sieves.

2. Description of the Prior Art

Both inositol and sorbitol are sugar alcohols which have higher market value than do the common sugars. Inositol is a generic name for a family of cyclohexanehexols (hexahydroxycyclohexane $C_6H_6(OH)_6$, in which there are nine possible stereoisomers. Of these possible isomeric forms, one occurs in predominance in nature and is known by various names including meso -inositol, myo -inositol, i -inositol, inosite, dambose, meat sugar or muscle sugar. Myo -inositol is a commercially important compound and has certain physiological activities. It is a member of the Vitamin-B complex, in which role it possesses activity as a growth factor for certain animals and microorganisms. It also is a factor in the regulation of fat and cholesterol metabolism in higher animals. For convenience purposes only, myo -inositol will be hereinafter referred to simply as inositol. In addition, although the present invention has been shown to be useful for the separation of myo -inositol, it is expected that some other inositol isomers, other than myo -inositol, could also be separated by the same process. For a more complete description of inositol and its properties, see Kirk-Othmer Encyclopedia of Chemical Technology, 2d Ed., Vol. 11 (1966), pp. 673–676.

No commercial process for the synthetic production of inositol is known to the present inventors. However, because it widely exists in living cells, it is possible to extract inositol from plants. Inositol exists in the free form in many fruits; for example, about 8 weight % of the soluble carbohydrates in almond hulls is inositol and about 1.2 weight % of the fresh weight of the berries of Loranthacene is inositol. Inositol also exists as the hexaphosphate (i.e., phytic acid) in the seeds of many plants. For example, about 2 weight % of corn "steepwater" solids (a by-product of the wet milling of corn) is phytic acid and inositol is currently commercially produced by recovery from such corn steepwater. Specifically, the phytic acid, which has the following composition (as the acid) $C_6H_6(OPO[OH]_2)_6$, is first precipitated out as a calcium/magnesium salt. The salt is hydrolyzed to inorganic phosphate and inositol, the inorganic phosphate is removed by precipitation and the inositol recovered by repeated crystallization. This process is both expensive and onerous, involving digestion at 100°–200° C. in strong acids or bases, etc.

Sorbitol may be made by the reduction of sugars and is an important commercial polyhydric alcohol in its pure form. Sorbitol has many uses, for example as a humectant in cosmetics or it may be used to make polyethers which are useful in plastics.

Commonly-assigned copending U.S. patent application Ser. No. 329,608, filed Dec. 10, 1981, now abandoned, discloses a process for the liquid phase separation of sorbitol and mannitol by selective adsorption on certain types of zeolite molecular sieves. Specifically, Table II at page 7 thereof, discloses selectivity for sorbitol by several cation forms of type X and type Y zeolites.

SUMMARY OF THE INVENTION

The present invention, in its broadest aspects, is a process for the liquid phase separation of inositol and/or sorbitol from solutions containing same by selective adsorption on cation-exchanged type X or type Y zeolite molecular sieves. The process generally comprises contacting the solution at a pressure sufficient to maintain the system in the liquid phase with an adsorbent composition comprising at least one crystalline aluminosilicate zeolite selected from the group consisting of zeolite type X and zeolite type Y wherein the zeolitic cations are selected from the group consisting of sodium, barium and calcium, to selectively adsorb inositol and/or sorbitol thereon; removing the non-adsorbed portion of the solution from contact with the adsorbent; and desorbing the adsorbate therefrom by contacting the adsorbent with a desorbing agent and recovering the desorbed inositol and/or sorbitol.

DESCRIPTION OF THE PREFERRED EMBODIMENTS

The present invention provides a process for the bulk separation of inositol and/or sorbitol from feed solutions containing same. The feed solution may be, for example, a mixture of sugars and/or sugar alcohols such as the liquid extract of fruit; or the feed may comprise a mixture of just sugar alcohols or a mixture of inositol and/or sorbitol with other carbohydrates. The solvent used to prepare the solution feedstock is not a critical factor, and can be any material which has a reasonable capacity to dissolve the carbohydrate species involved, is a liquid and is chemically inert toward the adsorbent and the essential solute compounds under the adsorption conditions imposed in carrying out the separation process. Water is the preferred solvent, but alcohols, ketones, esters and the like can be employed.

The present inventors have been informed of a proposed process which, in part, applies the selective adsorption aspects of the present invention to recover inositol from almond hulls by treating an aqueous extract thereof. Since inositol can constitute as much as about 8 weight percent of the soluble carbohydrates in almond hulls, an aqueous extract thereof, which also contains significant quantities of sorbitol, sucrose, glucose, and fructose, is a preferred feedstock for use in the process of the invention when the adsorbent has a marked preference for inositol or sorbitol. While the present invention is generic with respect to the feedstocks which can be suitably treated, the specific embodiment utilizing almond hull extract as the feedstock is not a species invention of ours.

The carbohydrates which along with inositol and/or sorbitol comprise the solutions suitably treated using the present process are well known in the art, are any of the well-known monosaccharides, disaccharides and even polysaccharides of which lactose, maltose, sucrose, mannose, galactose, allulose, fructose, sorbose and starch are representative. Other sugar alcohols such as mannitol, xylitol, ribitol and iditol can also be present and are considered to be carbohydrates for purposes of the present invention although they are not, strictly speaking, true carbohydrates.

Zeolite molecular sieves (hereinafter "zeolites") are crystalline aluminosilicates which have a three-dimensional framework structure and contain exchangeable cations. The number of cations per unit cell is determined by its silica-to-alumina ratio and the cations are distributed in the channels of the zeolite framework. Carbohydrate molecules can diffuse into the zeolite channels, and then interact with the cation and be adsorbed onto the cations. The cations are, in turn, attracted by the aluminosilicate framework which is a gigantic, multiply-charged anion. The adsorption selectivity of the zeolite depends on the concerted action of the electrostatic field intensity, cation radius, channel size, channel shape, and the density and spacial distribution of the cations. Since steric effects play a major role, the adsorption selectivities of zeolites are highly unpredictable.

We have found that although most zeolites do not adsorb inositol particularly strongly, NaX, BaX, and BaY zeolites do adsorb inositol substantially more strongly than sucrose, fructose, glucose, or sorbitol. Therefore, they are particularly suitable for inositol recovery. It also has been discovered that CaX and CaY zeolites have different adsorption selectivities for the above-mentioned five carbohydrates, but sorbitol, not inositol, is the most strongly adsorbed compound. CaX has the selectivity sequence of sorbitol>>inositol>fructose>glucose>sucrose. CaY has the selectivity sequence of sorbitol>>inositol≅fructose>glucose>sucrose. The distinctive selectivities of CaX allow the adsorbent to be used to isolate both sorbitol and inositol from the other three compounds by chromatographic elution. However, although CaY by itself may be used to separate sorbitol, it cannot easily isolate inositol in pure form. It must be used together with another adsorbent which can separate inositol from fructose.

Zeolite Y and the method for its manufacture are described in detail in U.S. Pat. No. 3,130,007, issued Apr. 21, 1954 to D. W. Breck. Zeolite X and the method for its manufacture are described in detail in United States Pat. No. 2,882,244, issued Apr. 14, 1959 to R. M. Milton. The disclosures of both of said patents are hereby incorporated herein by reference.

The type X and type Y zeolites useful in the present invention are those whose zeolitic cations are predominately sodium, barium or calcium; that is, these zeolites may contain a minor amount of another cation as long as the zeolite is capable of effecting the desired separation. For example, the calcium or barium exchanged zeolites may be prepared from a sodium exchanged zeolite using known techniques, and the product may contain a minor amount of sodium and still be useful in the present invention. Similarly, other cations such as potassium may be added to the zeolites in small amounts or be present as impurities without adversely affecting the usefulness of these zeolites in the present invention. More specifically, it is preferred that at least about 50%, and most preferably at least about 70%, on a charge equivalent basis, of the $AlO_4$ tetrahedra of the type X or type Y zeolite are electrovalently satisfied with the specified cation.

The adsorption affinities of various zeolites for different carbohydrates was determined by a "pulse test". This test consisted of packing a column with the appropriate zeolite, placing it in a block heater to maintain constant temperature, and eluting solutions through the column with water to determine the retention volume of solute. The retention volume of solute is defined as elution volume of solute minus "void volume". "Void volume" is the volume of solvent needed to elute a non-sorbing solute through the column. A soluble polymer of fructose, inulin, which is too large to be sorbed into the zeolite pores, was chosen as the solute to determine void volume. The elution volume of inulin was first determined. The elution volumes of the five above-identified carbohydrates were then determined under similar experimental conditions. The retention volumes were calculated and are recorded in Table I, below.

$\alpha_{Glucose}^{Inositol}$ (i.e., S.F.$_{I/G}$), $\alpha_{Fructose}^{Inositol}$ (i.e., S.F.$_{I/F}$), $\alpha_{Sucrose}^{Inositol}$ (i.e., S.F.$_{I/Su}$)

and $\alpha_{Sorbitol}^{Inositol}$ (i.e., S.F.$_{I/So}$)

From the retention volume data, the separation factors (S.F.), were calculated in accordance with the following typical equation:

$$S.F._{I/G} = \alpha_{Glucose}^{Inositol} = \frac{(\text{retention volume for inositol peak})}{(\text{retention volume for glucose peak})}$$

A S.F.$_{I/G}$ factor greater than unity indicates that the particular adsorbent was selective for inositol over glucose and similarly for the other separation factors shown in Table II. The separation factor values calculated according to the above-mentioned method are found in Table II.

TABLE I

CORRECTED RETENTION VOLUMES OF CARBOHYDRATES
(in ml's)

| Column Dimension: | 15.75 inches × 0.30 inch I.D. | | | | | | |
|---|---|---|---|---|---|---|---|
| Flow Rate: | 0.53 gpm/ft² | | | | | | |
| Temperature: | 160° F. | | | | | | |
| Zeolite Form: | powder | | | | | | |

| Zeolite | Mole Ratio | Inulin | Glucose | Fructose | Sucrose | Sorbitol | Inositol | Mannitol |
|---|---|---|---|---|---|---|---|---|
| NaX | 2.5 | 0 | 2.7 | 3.1 | 0.9 | 2.2 | 8.7 | 2.2 |
| NaY | 5.0 | 0 | 1.7 | 2.6 | 1.6 | 1.9 | 2.9 | 1.8 |

TABLE I-continued
CORRECTED RETENTION VOLUMES OF CARBOHYDRATES
(in ml's)

Column Dimension: 15.75 inches × 0.30 inch I.D.
Flow Rate: 0.53 gpm/ft$^2$
Temperature: 160° F.
Zeolite Form: powder

| Zeolite | Mole Ratio | Inulin | Glucose | Fructose | Sucrose | Sorbitol | Inositol | Mannitol |
|---|---|---|---|---|---|---|---|---|
| CaX | 2.5 | 0 | 0.3 | 1.9 | <0.2 | 12.8 | 5.2 | 13.0 |
| CaY | 5.0 | 0 | 1.7 | 7.3 | 0.2 | 27.0 | 6.7 | 20.9 |
| BaX | 2.5 | 0 | 3.6 | 7.4 | 0.3 | 22.0 | 34.6 | 10.5 |
| BaY* | 5.0 | 0 | 5.0 | 6.2 | 2.1 | 12.3 | 28.1 | 14.6 |
| NaY | 3.7 | 0 | 1.7 | 1.5 | 0.2 | <0.2 | 4.0 | 1.3 |

*the BaY zeolite was in the form of 30 × 50 mesh

TABLE II
SEPARATION FACTORS OF CARBOHYDRATES

| Zeolite | Mole Ratio | $\alpha_{Glucose}^{Inositol}$ | $\alpha_{Fructose}^{Inositol}$ | $\alpha_{Sucrose}^{Inositol}$ | $\alpha_{Sorbitol}^{Inositol}$ | $\alpha_{Mannitol}^{Inositol}$ |
|---|---|---|---|---|---|---|
| NaX | 2.5 | 3.2 | 2.8 | 9.7 | 4.0 | 4.0 |
| CaX | 2.5 | 17.3 | 2.7 | >26 | 0.4 | 0.4 |
| CaY | 5.0 | 3.9 | 0.9 | 33.5 | 0.2 | 0.3 |
| BaX | 2.5 | 9.6 | 4.7 | 115.0 | 1.6 | 3.3 |
| BaY | 5.0 | 5.6 | 4.4 | 13.4 | 2.3 | 1.9 |
| NaY | 5.0 | 1.7 | 1.1 | 1.8 | 1.5 | 1.6 |
| NaY | 3.7 | 2.4 | 2.7 | 20 | >20 | 3.1 |

By a similar technique, retention volumes and separation factors for inositol and various carbohydrates were obtained using a NaX zeolite (mole ratio, SiO$_2$/Al$_2$O$_3$, of 2.5) and the results are shown in Table III below:

TABLE III
Corrected Retention Volumes and Separation Factors of NaX

Column Dimension: 15.75 inches × 0.30 inch I.D.
Flow Rate: 0.53 gpm/ft$^2$
Temperature: 160° F.
Zeolite Form: powder

| Carbohydrate | Corrected Retention Volume (in ml's) | $\alpha_{Carbohydrate}^{Inositol}$ |
|---|---|---|
| Inulin | 0.0 | — |
| L-Arabinose | 2.0 | 4.4 |
| D-Galactose | 1.0 | 8.7 |
| D-Mannose | 1.5 | 5.8 |
| D-Ribose | 0.0 | >43.0 |
| D-Xylose | 1.0 | 8.7 |
| D-Cellobiose | 0.0 | >43.0 |
| D-Raffinose | 1.2 | 7.3 |
| D-Xylitol | 2.2 | 4.0 |
| Inositol | 8.7 | 1.0 |

In separating inositol and/or sorbitol from the other carbohydrates in solutions by the process of the present invention, a bed of solid zeolite adsorbent is preferentially loaded with adsorbates, the unadsorbed or raffinate mixture is removed from the adsorbent bed, and the adsorbed inositol and/or sorbitol is then desorbed from the zeolite adsorbent by a desorbant. The adsorbent can, if desired, be contained in a single bed, a plurality of beds in which conventional swing-bed operation techniques are utilized, or a simulated moving-bed countercurrent type of apparatus, depending upon the zeolite and upon which of inositol and/or sorbitol is being adsorbed. Thus, one can employ a chromatographic elution method (such as that described in U.S. Pat. No. 3,928,193, the disclosure of which is hereby incorporated herein by reference) to recover each of the five above-identified carbohydrates in pure form, including inositol. As the zeolite adsorbent, BaX, BaY, NaX and CaX can be used. CaY cannot be used by itself, since the inositol/fructose separation must be accomplished by a second bed, which may contain any of CaX, NaX, BaX or BaY.

Based on the data in Tables I and II, it is generally preferred that the sodium forms of zeolite types X and Y have a lower silica to alumina ratio since such zeolites generally enable higher separation factors to be achieved.

A preferable method for practicing the process of this invention is separation by chromatographic column. In this method, feedstock solution is injected for a short period of time at the top of a column and eluted down through the column with water. As the mixture passes through the column, chromatographic separation leads to a zone increasingly enriched in the adsorbed carbohydrate. The degree of separation increases as the mixture passes further down through the column until a desired degree of separation is achieved. At this point, the effluent from the column may be first shunted to one receiver which collects a pure product. Next, during the period of time when there is a mixture of carbohydrates emerging from the column, the effluent may be directed towards a "receiver for mixed product". Next, when the zone of adsorbed carbohydrate emerges from the end of the column, the effluent may be directed to a receiver for that product.

As soon as the chromotagraphic bands have passed far enough through the column, a new slug is introduced at the entrance of the column and the whole process cycle is repeated. The mixture which exits from the end of the column between the times of appearance of the pure fractions is recycled back to the feed and passed through the column again, to extinction.

The degree of separation of the peaks as they pass through this chromatographic column will increase as the column length is increased. Therefore, one can design a column of sufficient length to provide any desired degree of separation of the two components from each other.

Therefore, it is also possible to operate such a process in a mode which will involve essentially no recycle of an unseparated mixture back to the feed. However, if high purities are required, such a high degree of separation may require an exceptionally long column. In addition, as the components are eluted through the column, their average concentrations gradually decline. In the case of the carbohydrates being eluted with water, this would mean that the product streams would be increasingly diluted with water. Therefore, it is highly likely that an optimum process (to achieve high degrees of purity of the components) should involve the use of a much shorter column (than would be required for complete separation of the peaks) and also involve separating out the portion of the effluent containing the mixture of peaks and recycling it to feed, as discussed above.

It is also possible to use NaX, BaX and BaY in a simulated moving bed process (e.g., as described in U.S. Pat. No. 2,985,589, the disclosure of which is hereby incorporated herein by reference). However, it is impossible to use CaX or CaY alone in a single-stage simulated moving bed process to produce pure inositol when sorbitol is also present because for such a process only the least strongly adsorbed or most strongly adsorbed adsorbate can be produced in pure form. However, it is possible to design a two-stage process using, for example, CaX in the first stage to separate (inositol+sorbitol) in one cut (from sucrose+fructose+glucose), and then to use CaY in the second stage to separate inositol from sorbitol.

In the operation of a simulated moving-bed technique, the selection of a suitable displacing or desorbing agent or fluid (solvent) must take into account the requirements that it be capable of readily displacing adsorbed carbohydrate from the adsorbent bed and also that carbohydrate from the feed mixture be able to displace adsorbed desorbing agent from a previous adsorption step. Further, the desorbing agent employed should be readily separable from admixture with the carbohydrate components of the feed-stock. Therefore, it is contemplated that a desorbing agent having characteristics which allow it to be easily fractionated from the carbohydrate should be used. For example, volatile desorbing agents should be used, such as alcohols, ketones, water, mixtures thereof, mixtures of alcohols and water, particularly methanol and ethanol, etc. The most preferred desorbing agent is water.

BaX and BaY are very strong adsorbents for inositol, which makes them particularly suitable for recovery of inositol in those cases where inositol is a relatively minor component in the mixture, and its concentration is low. This strong affinity means high adsorption capacity, even at low concentrations. However, the strong affinity also means a very broad desorption front. In this case, it may well be attractive economically to use a fixed bed adsorption/desorption process. In this type of process, the feed is allowed to flow through the bed until most of the bed is saturated with inositol. Then, the bed is desorbed. The fraction of effluent which contains pure inositol is collected as the product and the fraction which contains contaminated inositol is recycled.

Various modifications of this process are possible and will be obvious to those skilled in the art. For example, after loading the BaX or BaY bed to near the point at which inositol begins to break through and appear in the effluent, the feed can be switched to a co-current stream of pure inositol in water, which can be passed through the bed to displace the non-inositol components from the sorbent and from the void spaces in the bed. When these non-inositol components have been adequately displaced from the bed, the bed can be counter-currently desorbed with water to recover the inositol from the sorbent and voids. This type of fixed bed loading/co-product purge/counter-current desorption cycle may be particularly attractive when the inositol is present at low concentrations and it is desired to recover it at higher purity levels.

NaX is also a particularly suitable adsorbent for inositol recovery, because of its unique, high selectivity for inositol. Though its loading capacity is not as high as BaX and BaY, the desorption of inositol from NaX is faster than from BaX and BaY. Thus, NaX can be used for a separation process which has a shorter cycle time than BaX and BaY, and will be suitable for both fixed bed and simulated moving bed processes.

While it is possible to utilize the activated adsorbent zeolite crystals in a non-agglomerated form, it is generally more feasible, particularly when the process involves the use of a fixed adsorption bed, to agglomerate the crystals into larger particles to decrease the pressure drop in the system. The particular agglomerating agent and the agglomeration procedure employed are not critical factors, but it is important that the bonding agent be as inert toward the carbohydrates being adsorbed and desorbing agent as possible. The proportions of zeolite and binder are advantageously in the range of 4 to 20 parts zeolite per part binder on an anhydrous weight basis.

The temperature at which the adsorption step of the process should be carried out should be from about 0° to 150° C. As the temperature increases, the temperature at which the desorbent boils will be reached. Preferably, the adsorption step should take place between about 15° C. and about 100° C. Pressure conditions must be maintained so as to keep the system in liquid phase. High process temperatures needlessly necessitate high pressure apparatus and increase the cost of the process.

Figure 5:
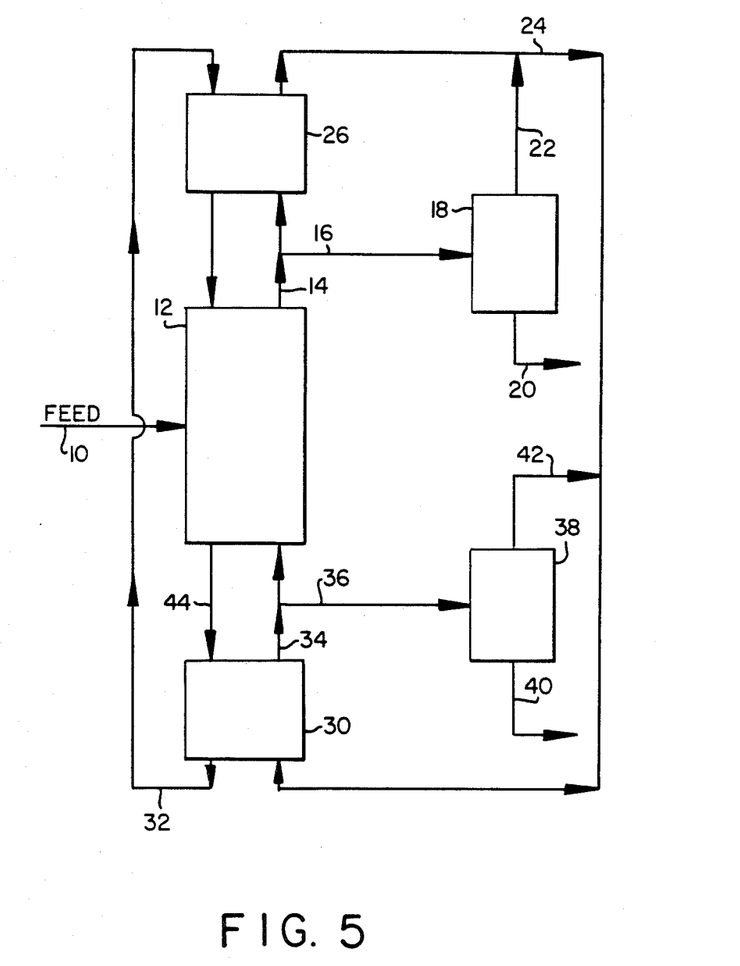
FIG. 5 shows one method in which the process of this invention may be employed.

Another method for practicing the process of this invention is illustrated by the drawing in FIG. 5. In this method, a number of fixed beds are connected to one another by conduits which are also connected to a special valve (e.g., of the type described in U.S. Pat. No. 2,985,589). The valve sequentially moves the liquid feed and product takeoff points to different positions around a circular array of the individual fixed beds in such a manner as to simulate countercurrent motion of the adsorbent. This process is well-suited to binary separations.

In the drawings, FIG. 5 represents a hypothetical moving-bed countercurrent flow diagram involved in carrying out a typical process embodiment of the present invention. With reference to the drawing, it will be understood that whereas the liquid stream inlets and outlets are represented as being fixed, and the adsorbent mass is represented as moving with respect to the counter flow of feedstock and desorbing material, this representation is intended primarily to facilitate describing the functioning of the system. In practice, the sorbent mass would ordinarily be in a fixed bed with the liquid stream inlets and outlets moving with respect thereto. Accordingly, a feedstock is fed into the system through line 10 to adsorbent bed 12 which contains particles of zeolite adsorbent in transit downwardly therethrough. The temperature is at 70° C. throughout the entire system and the pressure is substantially atmospheric. The component(s) of the feedstock are adsorbed preferentially on the zeolite particles moving through bed 12, and the raffinate is entrained in the liquid stream of water desorbing agent leaving bed 12 through line 14 and a major portion thereof is withdrawn through line 16 and fed into evaporation apparatus 18 wherein the mixture is fractionated and the concentrated raffinate is discharged through line 20. The water desorbing agent leaves the evaporation apparatus 18 through line 22 and is fed to line 24 through which it is admixed with additional desorbing agent leaving the adsorbent bed 26, and is recycled to the bottom of adsorbent bed 30. The zeolite carrying adsorbed carbohydate passes downwardly through line 44 into bed 30 where it is counter-currently contacted with recycled desorbing agent which effectively desorbs the carbohydrate therefrom before the adsorbent passes through bed 30 and enters line 32 through which it is recycled to the top of adsorbent bed 26. The desorbing agent and desorbed carbohydrate leave bed 30 through line 34. A portion of this liquid mixture is diverted through line 36, where it passes evaporation apparatus 38, and the remaining portion passes upwardly through adsorbent bed 12 for further treatment as hereinbefore described. In evaporation apparatus 38, the desorbing agent and carbohydrate are fractionated and the carbohydrate product is recovered through line 40 and the desorbing agent is either disposed of or passed through line 42 into line 24 for recycle as described above. The undiverted portion of the desorbing agent/raffinate mixture passes from bed 12 through line 14, enters bed 26 and moves counter-currently upwardly therethrough with respect to the desorbing agent-laden zeolite adsorbent passing downwardly therethrough from recycle line 32. The desorbing agent passes from bed 26 in a relatively pure form through recycle line 24 and to bed 30 as hereinbefore described.

The following Examples are provided to illustrate the present invention. However, they do not limit the invention to the embodiments in the Examples. All examples are based on actual experimental work. As used in the Examples appearing below, the following abbreviations and symbols have the indicated meaning:
NaX = Sodium-exchanged zeolite X
NaY = Sodium-exchanged zeolite Y
BaX = Barium-exchanged zeolite X
gpm/ft² = gallons per minute per square foot.

EXAMPLE 1

Figure 1:
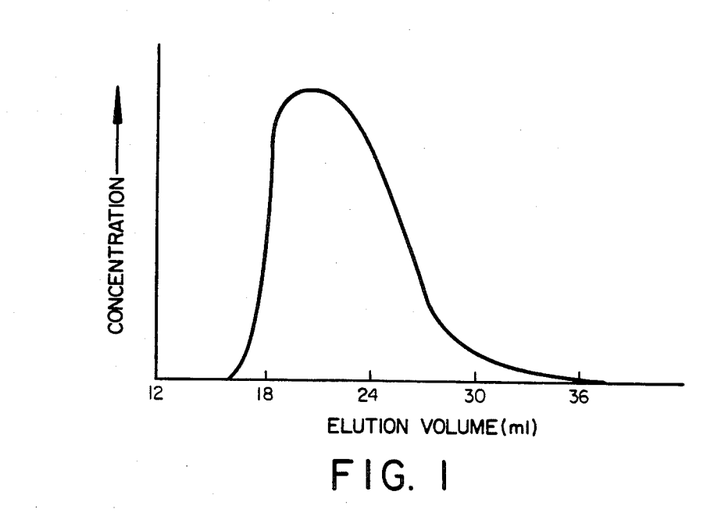
FIG. 1 shows an elution curve of a mixture of sugars and sugar alcohols where the adsorbent is a sodium-substituted zeolite type Y.

A 15.75 inch column having an inside diameter of 0.3 inch was loaded with NaY zeolite powder ($SiO_2/Al_2O_3$ mole ratio = 5.0). The column was filled with water and maintained at a temperature of 160° F. Water was then pumped through the column and a flow rate of 0.53 gpm/ft² was maintained. For a period of one minute, the feed was switched to a mixture which contained 3.9% glucose, 3.7% fructose, 0.6% sucrose, 1.0% sorbitol and 0.8% inositol, and then switched back to water. The composition of the effluent from the column was monitored by a refractive index detector. A refractive index detector cannot differentiate one carbohydrate from another, but it does detect the presence of carbohydrate in the effluent. Such detectors are most useful where each component emerges in the effluent as completely separate peaks. The identity of each peak then can be determined by its characteristic retention volume. However, such detection techniques can also be useful to demonstrate a column or conditions which lack separation power for certain mixtures. Under such circumstances, the mixture will emerge as a single peak with a narrow peak width. FIG. 1 of the drawings shows the elution curve for the above five-component mixture which emerged from the NaY column as a single peak. The observed single peak indicates that the separation ability of this NaY zeolite was insufficient under the above conditions to allow resolution of the inositol or other components into separate peaks. However, based upon the data in Table I, supra, it is apparent that this single peak is the sum of separate peaks attributable to each component. Furthermore, those skilled in the art will realize that by using different conditions (e.g., a longer column, slower flow rate, smaller zeolite powder, different feed such as without fructose a different detector, etc.) it would be possible to obtain an observable separation using this NaY zeolite (compare the results in Example 4, infra, where NaX separated inositol into a completely separate peak under similar experimental conditions).

EXAMPLE 2

Figure 2:
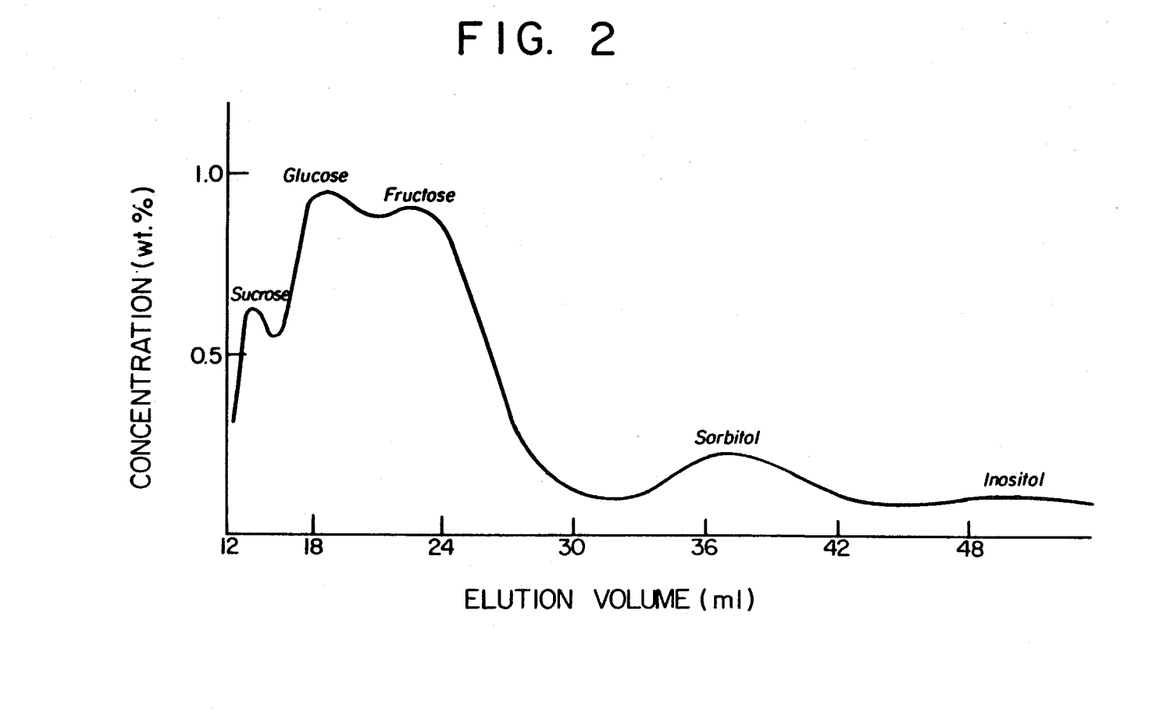
FIGS. 2–4 show elution curves of the same sugar-sugar alcohol mixture where the adsorbents are barium-substituted, barium-substituted and sodium-substituted zeolite type X adsorbents, respectively.

The same column and experimental conditions as in Example 1 were used except that the zeolite used was BaX powder ($SiO_2/Al_2O_3$ mole ratio = 2.5). FIG. 2 gives the elution curves. The elution order is: sucrose, glucose, fructose, sorbitol and inositol. Inositol is well separated from all other carbohydrates.

EXAMPLE 3

Figure 3:
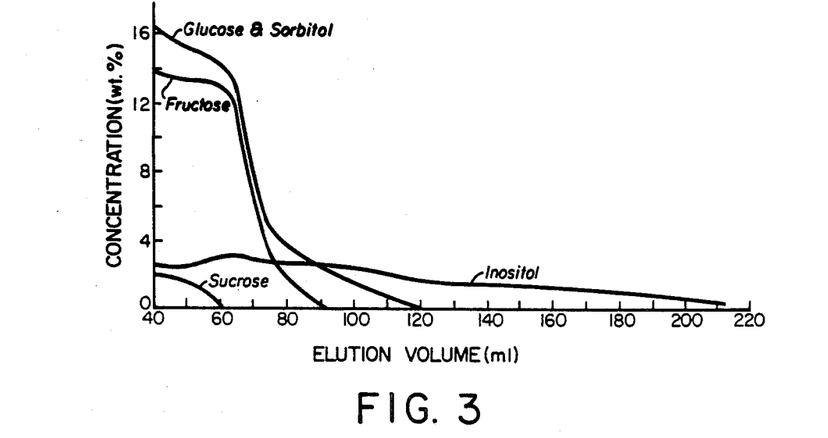

A 63 inch column having an inside diameter of 0.3 inch was loaded with BaX zeolite ($SiO_2/Al_2O_3$ mole ratio = 2.5)(30×40 mesh particles), and maintained at 160° F. The column was loaded with a feed which contained 15.6% glucose, 14.8% fructose, 2.4% sucrose, 4.0% sorbitol and 3.2% inositol. After the column reached equilibrium, the regeneration started. Water was used as a desorbent and was pumped through at a flow rate of 0.27 gallons per minute. The effluent was collected and analyzed by liquid chromatography. The results are shown in FIG. 3. 80 cc of pure inositol at an average concentration of 1 wt % was collected.

EXAMPLE 4

Figure 4:
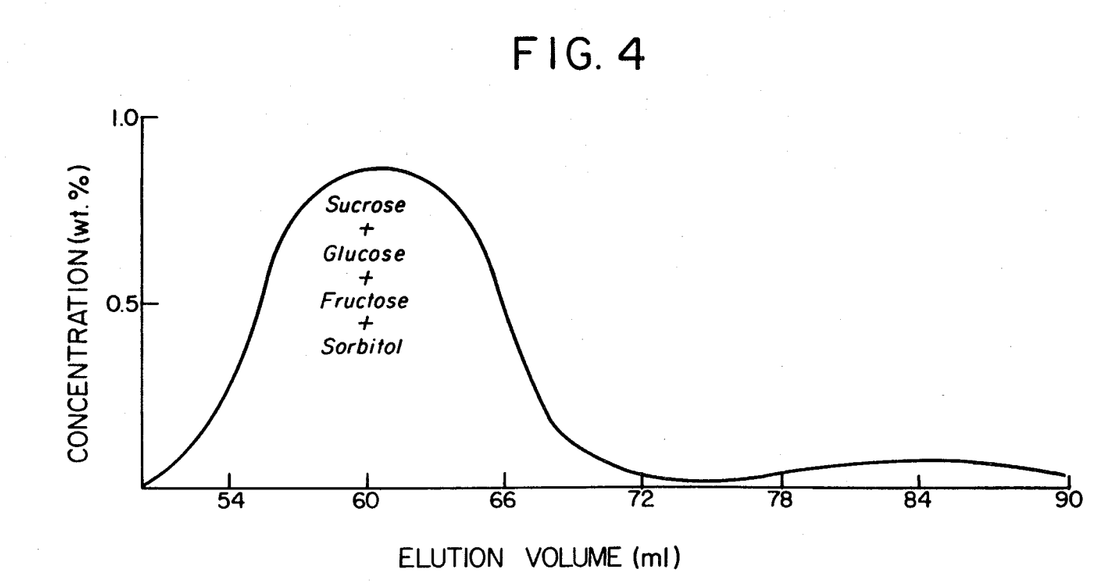

The same column used in Example 3 was loaded with NaX zeolite ($SiO_2/Al_2O_3$ mole ratio = 2.5)(30×40 mesh particles), and maintained at 160° F. The column was subjected to the same experiment as described in Example 1. FIG. 4 gives the elution curves. Sorbitol, sucrose, glucose and fructose emerge as one peak. Inositol emerges as the second peak, which is well separated from the first one.

We claim:

1. A process for separating sorbitol from a solution of a carbohydrate mixture also containing inositol by selective adsorption which comprises contacting said solution at a temperature of from about 0° C. to 150° C. and at a pressure sufficient to maintain the system in the liquid phase with an adsorbent composition comprising at least one crystalline aluminosilicate zeolite selected from the group consisting of zeolite type Y and zeolite type X in which the zeolite cations in association with at least 50% of the $AlO_4$ tetrahedra of said aluminosilicate are calcium, whereby the sorbitol is selectively adsorbed thereon, removing the non-adsorbed portion of said solution from contact with the zeolite adsorbent, and desorbing the sorbitol therefrom by contacting said adsorbent with a desorbing agent and recovering the desorbed sorbitol.

2. Process according to claim 1 wherein the crystalline aluminosilicate zeolite is zeolite type Y.

3. Process according to claim 2 wherein the temperature is from about 17° C. to 100° C.

4. Process according to claim 3 wherein the desorbent is selected from the group consisting of alcohols, ketones, water and mixtures thereof.

5. Process according to claim 1 wherein the carbohydrate mixture comprises sorbitol, inositol and at least one sugar wherein in a first stage said solution is contacted at a temperature of from about 0° C. to 150° C. and at a pressure sufficient to maintain the system in the liquid phase with an adsorbent composition comprising at least one crystalline aluminosilicate zeolite of type X in which the zeolite cations are calcium, whereby a mixture of inositol and sorbitol are selectively adsorbed, removing the non-adsorbed portion of said solution from contact with the zeolite adsorbent, desorbing the mixture of inositol and sorbitol therefrom by contacting said adsorbent with a desorbing agent; contacting in a second stage said mixture at a temperature of from about 0° C. to 150° C. and at a pressure sufficient to maintain the system in the liquid phase with an adsorbent composition comprising at least one crystalline aluminosilicate zeolite of type Y in which the zeolite cations are calcium, whereby first sorbitol and then inositol are selectively adsorbed, removing the non-adsorbed portion of said mixture from contact with the zeolite adsorbent and desorbing first inositol and then sorbitol therefrom by contacting said adsorbent with a desorbing agent and recovering first the desorbed sorbitol and then the desorbed inositol.

6. Process according to claim 3 wherein said carbohydrate mixture comprises at least one sugar and at least one sugar alcohol.

* * * * *